United States Patent
Migonney et al.

(10) Patent No.: US 9,139,678 B2
(45) Date of Patent: Sep. 22, 2015

(54) METHOD FOR GRAFTING BIOACTIVE POLYMERS ON PROSTHETIC MATERIALS

(75) Inventors: Véronique Migonney, Eaubonne (FR); Gérard Helary, Santeuil (FR); Flavie Noirclere, Saint-Cloud (FR)

(73) Assignee: UNIVERSITE PARIS 13, Villetaneuse (FR)

( * ) Notice: Subject to any disclaimer, the term of this patent is extended or adjusted under 35 U.S.C. 154(b) by 1124 days.

(21) Appl. No.: 12/227,935

(22) PCT Filed: Jun. 7, 2007

(86) PCT No.: PCT/FR2007/051389
§ 371 (c)(1),
(2), (4) Date: Aug. 26, 2009

(87) PCT Pub. No.: WO2007/141460
PCT Pub. Date: Dec. 13, 2007

(65) Prior Publication Data
US 2009/0318622 A1 Dec. 24, 2009

(30) Foreign Application Priority Data
Jun. 7, 2006 (FR) .................................... 06 05073

(51) Int. Cl.
C08F 292/00 (2006.01)
C08L 51/10 (2006.01)
A61L 27/06 (2006.01)
A61L 27/34 (2006.01)
A61F 2/28 (2006.01)
A61C 8/00 (2006.01)
A61K 6/083 (2006.01)
A61K 6/04 (2006.01)
A61F 2/32 (2006.01)
A61L 27/50 (2006.01)
C08F 291/00 (2006.01)
C08L 51/00 (2006.01)
C09D 4/00 (2006.01)
A61F 2/30 (2006.01)

(52) U.S. Cl.
CPC ............. *C08F 292/00* (2013.01); *A61C 8/0013* (2013.01); *A61C 8/0016* (2013.01); *A61F 2/28* (2013.01); *A61F 2/32* (2013.01); *A61K 6/04* (2013.01); *A61K 6/083* (2013.01); *A61L 27/06* (2013.01); *A61L 27/34* (2013.01); *A61L 27/50* (2013.01); *C08F 291/00* (2013.01); *C08L 51/003* (2013.01); *C08L 51/10* (2013.01); *C09D 4/00* (2013.01); *A61F 2002/30003* (2013.01); *A61F 2310/00023* (2013.01); *A61F 2310/00389* (2013.01)

(58) Field of Classification Search
CPC ......... C08F 292/00; C08L 51/10; A61F 2/28; A61F 2/32; A61F 2002/30003; A61F 2310/00023; A61F 2310/00389; A61L 27/06; A61L 27/34; A61C 8/0016; A61C 8/0013; A61K 6/04; A61K 6/083
USPC .......... 623/16.11, 18.11, 22.11, 23.53, 23.57, 623/23.59; 427/2.24, 2.26, 487, 495, 508, 427/327; 424/78.08, 78.18, 78.31, 78.37; 433/201.1, 206; 524/783; 525/330.3, 525/329.7, 328.5
See application file for complete search history.

(56) References Cited

U.S. PATENT DOCUMENTS

| | | | |
|---|---|---|---|
| 4,421,569 A | 12/1983 | Dichter et al. | |
| 5,607,475 A | 3/1997 | Cahalan et al. | |
| 5,782,908 A | 7/1998 | Cahalan et al. | |
| 5,804,263 A * | 9/1998 | Goldberg et al. | 428/34.7 |
| 2004/0144655 A1* | 7/2004 | Bertrand et al. | 205/235 |
| 2006/0136057 A1* | 6/2006 | Brulez et al. | 623/13.11 |

FOREIGN PATENT DOCUMENTS

| | | |
|---|---|---|
| CA | 2241483 | 6/1998 |
| CA | 2241483 | * 12/1998 |
| CA | 2 496 118 | 3/2004 |
| EP | 0 893 164 | 1/1999 |
| WO | WO 2004/067051 A1 * | 8/2004 |

OTHER PUBLICATIONS

International Search Report for PCT/FR2007/051389, mailed Nov. 30, 2007.
Li et al, "Improved biological performance of Ti implants due to surface modification by micro-arc oxidation", Biomaterials 25 (2004) 2867-2875.
Lim et al, "Surface Characterizations of Variously Treated Titanium Materials", The International Journal of Oral & Maxillofacial Implants 2001; 16:333-342.
Sul et al, "The bone response of oxidized bioactive and non-bioactive titanium implants", Biomaterials 26 (2005) 6720-6730.
Takemoto et al, "Platelet adhesion on titanium oxide gels: effect of surface oxidation", Biomaterials 25 (2004) 3485-3492.

* cited by examiner

*Primary Examiner* — Roberto Rabago
(74) *Attorney, Agent, or Firm* — Nixon & Vanderhye P.C.

(57) ABSTRACT

The invention concerns methods for grafting bioactive polymers on a prosthetic material, the materials obtainable by said method and applications thereof. More specifically, the invention concerns a method for directly grafting polymers on the surface of prosthetic materials.

8 Claims, 6 Drawing Sheets

METHOD FOR GRAFTING BIOACTIVE POLYMERS ON PROSTHETIC MATERIALS

Figure 1:
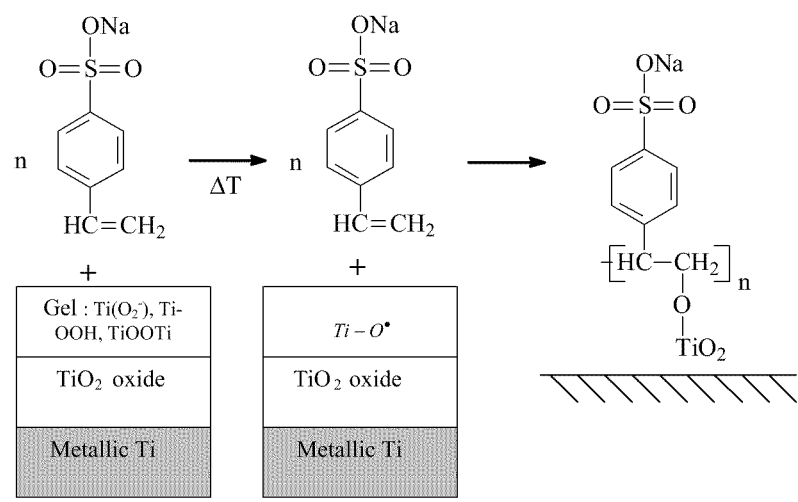

This application is the U.S. national phase of International Application No.
PCT/FR2007/051389, filed 7 Jun. 2007, which designated the U.S. and claims priority to France Application No. 06/05073, filed 7 Jun. 2006, the entire contents of each of which are hereby incorporated by reference.

The present invention relates to methods for grafting bioactive polymers onto a prosthetic material, to the materials that may be obtained via this method and to the applications thereof. More specifically, the invention relates to a method for the direct grafting of polymers onto the surface of prosthetic materials.

The implantation of a prosthesis into a bone site gives rise to a cascade of tissue/implant reactions known as the "host response", which, if it is controlled, may finally result in "osteointegration of the implant". Ostecintegration is the total integration of the implant into the bone by means of intimate bony tissue/prosthesis contact and by virtue of an absence of fibrous tissue at the interface. This integration is necessary in order to restore a deficient function via final bony implants (joint prostheses, dental implants). This method may, however, be affected by several parameters, firstly the physico-chemical properties of the material such as the surface topography, the roughness, the chemical composition and the surface energy, and secondly the surgical technique and the presence of microorganisms. Furthermore, the presence of "fibro-inflammatory" tissue around the implant, which has neither the biological activities nor the mechanical characteristics of bone tissue, increases the susceptibility to aseptic loosening (unfastening of the implant) and to infection of the site of the implantation.

At the present timer to ensure the anchoring of total hip prostheses into the bone, two approaches are commonly used: either the metallic implant (which may be coated with hydroxyapatite) is mechanically anchored by force into the bone, or it is fixed in using a cement based on poly(methyl methacrylate) (PMMA). In the last thirty years, "hydroxyapatite" coatings have been very widely used for improving the osteointegration of implants, since they allow good bone anchoring while at the same time offering good mechanical performance within a relatively short space of time.

Biomaterials are materials intended to totally or partially replace functions that can no longer be fulfilled by deficient tissues, a deficient organ or a deficient organ part. To do this, implantable biomaterials must mainly satisfy two criteria. They must first have specific mechanical properties, necessary to correctly ensure the mechanical functions of the defective tissues or organs. They must also not trigger any hostile response by the host, i.e. they must be "accepted" and integrated by the host in a controlled manner, in other words they must be "biointegratable".

However, no synthetic material currently implanted can really be considered as "biointegratable". The reason for this is that the implanted material is considered as a "foreign body" by the living system, and this triggers a series of events grouped under the term inflammatory response, which, if it is not controlled, may then finally lead to rejection of the implant. Moreover, this material considered as a "foreign body" appears as a favored support for the adhesion and colonization of microorganisms such as bacteria. The adhesion of potentially infectant bacteria onto biomedical implants being the initiating step of infection, this is thus a serious problem. Moreover, this bacterial adhesion is in many cases followed by the formation of a "biofilm" which plays a role of protecting the bacteria against any therapy and especially against antibiotics. For example, *staphylococcus* infections following the implantation of a permanent biomaterial (orthopedic prosthesis) or even a temporary biomaterial (catheter) often have dramatic consequences for the patients, for instance septicemia, endocarditis or osteomyelitis, and they are extremely difficult or even impossible to cure for as long as the implant remains in place. Thus, rejection during the implantation of a biomaterial into a living organism, and infection of the implanted materials, are all too often observed. These undesirable biological responses toward the implant may lead to a further surgical intervention, or even to the removal of the implanted biomaterial.

The biomaterial/cell interactions should thus be optimized in the case of joint implants, but also in the case of dental implants and, in parallel, the infection of these materials should be prevented by controlling the biomaterial/bacteria interactions.

Research has been conducted in order to improve the biocompatibility and the biointegration of the materials used as implants and, consequently, to reduce the hostile host responses leading to rejection of the implant. One research approach concerns the modification of the surfaces of prosthetic materials, in particular modification of the surface of titanium and of its alloys. The aim of such a modification is to promote the biointegration of the implants into bone tissue, while at the same time preventing infections.

A method for grafting polymers via silanization has been described. This method makes it possible to functionalize surfaces that are hydroxylated or rich in $NH_2$ prior to the grafting of a polymer. In the case of titanium, silanization was mainly used to create metal-polymer interfaces. The grafted polymers may be bioactive polymers, i.e. polymers that are capable of orienting eukaryotic and/or prokaryotic cell responses in the sense that such grafted polymers promote the osteointegration of a prosthetic implant and prevent the development of an infection.

The silanization protocol used on these substrates by the majority of authors consists in chemically attacking the surface of the sample to promote the presence of hydroxyl groups, and then in immersing the sample in a solution containing the silane molecule. The advantages of these reactions are their simplicity and their stability, which are attributed to their covalent bonding and to their network structure. However, the efficacy of the silanization depends on the concentration of hydroxyl groups at the surface of the material, and this technique does not allow all polymers to be immobilized, but only those bearing a functional group that is compatible with the one located at the end of the chain of the silane derivative.

The majority of authors thus use silanization as an intermediate step to the subsequent grafting of a bioactive or organic molecule. In the rest of the present patent application, this method of grafting via prior silanization will be referred to as an "indirect grafting method".

The present inventors have developed a novel method for grafting bioactive polymers onto a prosthetic material.

A first aspect of the invention thus concerns a method for grafting bioactive polymers onto a prosthetic material.

According to a second aspect, the invention relates to the prosthetic materials that may be obtained via such a method.

According to a final aspect, the invention relates to the prosthetic implants manufactured from the prosthetic materials that may be obtained via the method of the invention.

In the grafting method of the present invention, and unlike the indirect grafting method described above, no intermediate molecule, such as a silane derivative, is used between the surface of the material and the polymer to be grafted onto it.

Thus, one subject of the invention is a method for grafting bioactive polymers onto a prosthetic material, comprising the following steps:

free-radical-donating active species are generated at the surface of the prosthetic material; and the prosthetic material onto which active species have been generated is placed in contact with at least one monomer bearing a function that allows radical polymerization, its radical polymerization allowing the formation of a bioactive polymer, in the absence of oxygen.

The method according to the invention is a direct method, as opposed to the indirect method described above, in the sense that the polymers are formed directly on the prosthetic material from the monomers of which it is composed. Specifically, in the present method, free radicals are formed directly on the prosthetic material, which then serves as an initiator for the polymerization reaction.

The inventors have been able to show that such a direct grafting method has several advantages over the indirect grafting method. The method according to the invention is especially more economical, faster and more efficient than the indirect method, in particular in terms of amount of polymer bound to the prosthetic material. Thus, generally, the method of the present invention makes it possible to obtain a grafting density 2 to 15 times greater than that obtained with the indirect grafting method via silanization of the prior art.

As stated previously, the grafting method of the present invention is free of any intermediate step of grafting of an intermediate molecule between the prosthetic material and the grafted polymer.

For the purposes of the present invention, a prosthetic material is a material that can be used in the manufacture of a medical implant such as a prosthesis, in particular a hip prosthesis or a dental prosthesis.

The materials modified via the method of the present invention more specifically correspond to any material on the surface of which free radicals may be formed via chemical oxidation, especially via acidic chemical oxidation or via ozonization, followed by heating. In this respect, mention may be made especially of metal supports, including titanium and its alloys, especially based on nickel, vanadium, aluminum and/or molybdenum, aluminum, tantalum, iridium, zirconium, gold and steel, or based on ceramic or glass. In one particular embodiment of the invention, the prosthetic material is a nonpolymeric prosthetic material.

Advantageously, the prosthetic material is titanium or an alloy thereof.

Titanium is commonly used as a prosthetic material since it is biocompatible. Specifically, titanium is a material of choice for orthopedic or dental implants on account of its mechanical properties that are quite similar to those of bone, its good tolerance due to its osteointegration capacities and/or to the absence of allergic or rejection phenomena with respect to titanium.

Advantageously, the prosthetic material may be polished by abrasion before formation of the free radicals, to dispense with the problems of roughness of the surface of the material. Thus, in one particular embodiment of the invention, the prosthetic materials are polished with abrasive paper and preferably with different abrasive papers of decreasing granulometry. More specifically, the mechanical polishing of the prosthetic materials may be performed using an automated arm mounted on a rotary polisher, with abrasive paper of decreasing granulometries. Thus, abrasive papers of grade 800, 1000 and then 1200 may be successively used. The prosthetic material may also be washed, preferably following polishing, especially in an acetone solution, and then preferably dried. It may be used directly after the polishing, washing and/or drying step, or may be stored in the absence of oxygen, preferably under an inert atmosphere, such as under argon or helium.

Advantageously, the free-radical-donating active species are generated at the surface of the prosthetic material by oxidation, in particular by chemical oxidation. Mention may be made especially of chemical oxidation using an acid/$H_2O_2$ mixture, in particular $H_2SO_4/H_2O_2$, or oxidation by ozonization. Chemical oxidation by using an acid/$H_2O_2$ mixture is particularly preferred in the case of oxidation of metallic prosthetic materials, in particular the use of an $H_2SO_4/H_2O_2$ mixture. Other acids may also be used to form peroxides at the surface of the prosthetic material, especially hydrofluoric acid or hydrochloric acid, still as a mixture with $H_2O_2$.

The term "acid/$H_2O_2$ mixture" means the simultaneous or sequential mixing of solutions, namely the acid solution and the $H_2O_2$ solution. Thus, either the two solutions are simultaneously placed in contact with the prosthetic material to be oxidized, or the acid solution is placed in contact in a first stage, and the $H_2O_2$ solution is then placed in contact in a second stage with the prosthetic material. In any case, the oxidation time may vary within a wide range and a person skilled in the art can adapt it as a function of the prosthetic material to be treated, the mode of chemical oxidation used to form the free-radical-donating species at the surface of this material, and the desired grafting density. A person skilled in the art can especially determine the best procedure by measuring the degree of grafting obtained after having grafted polymers onto the oxidized prosthetic material to be tested, especially by assaying the grafting density with toluidine blue (see Example 1.5).

In the case of a simultaneous acid/$H_2O_2$ oxidation mixture, the oxidation time is preferably from 1 to 10 minutes and more preferably from 3 to 6 minutes, and the most preferred oxidation time is 5 minutes. Preferably, this oxidation time applies to the oxidation of titanium or an alloy thereof with an $H_2SO_4/H_2O_2$ solution.

In the case of using sequential mixing, the prosthetic material may be, for example, immersed in the acid solution for at least 10 seconds, preferably for at least 20 seconds, preferably for at least 30 seconds, more preferably for more than 50 seconds, preferably for more than 1 minute, preferably for more than 2 minutes, preferably for more than 3 minutes and preferably for more than 4 minutes. This contact time of titanium or an alloy thereof with $H_2SO_4$ may be considerably longer and may be up to, for example, 30 minutes or more. However, in one preferred embodiment, the contact time of the prosthetic material with the acid solution is less than or equal to 5 minutes, beyond which time a decrease in the degree of grafting is observed. This procedure is in particular applied in the case of the oxidation of titanium or an alloy thereof, placed in contact with an $H_2SO_4$ solution.

Similarly, the contact time of the prosthetic material with the $H_2O_2$ solution may vary. Preferably, the prosthetic material, preferably titanium or an alloy thereof, is placed in contact with $H_2O_2$ for at least 10 seconds, preferably for at least 20 seconds, preferably for at least 30 seconds, preferably for at least 40 seconds, preferably for at least 50 seconds, preferably for at least 1 minute, preferably for at least 2 minutes, preferably for 2 to 3 minutes and most preferably for 2 minutes after adding the $H_2O_2$ solution. In one preferred embodiment, an action of $H_2SO_4$ on titanium, or an alloy thereof, for 1 minute followed by an action of $H_2O_2$ on titanium for 2 minutes is preferred.

The placing in contact of the prosthetic material with the acid solution and/or the $H_2O_2$ solution may be performed via any means known per se. Thus, for example, the solutions may be poured into a container containing the prosthetic material, or the prosthetic material may be immersed in a container containing the solution(s).

Without wishing to be bound by any theory, the inventors believe that the treatment with an acid solution makes it possible to remove the native oxide layer that spontaneously forms on the prosthetic materials in the presence of air, by attacking it chemically. The hydrogen peroxide creates hydro-peroxides at the surface of the prosthetic material, in particular titanium hydroperoxides (TiOOH) in the case of the use of titanium as prosthetic material. These hydroperoxides, which donate free radicals when they are heated, can then serve as initiators for the radical polymerization of the monomers on the prosthetic material, in particular on titanium.

The proportion of acid relative to $H_2O_2$ may vary within a wide range and a person skilled in the art is capable of defining, on the basis of the present description, the most efficient ratio for achieving a desired degree of grafting.

Preferably, a 50/50 (v/v) $H_2SO_4/H_2O_2$ solution is used to oxidize the prosthetic material. The temperature used is generally room temperature (20-30° C.), or even a lower temperature (for example between 0 and 20° C.) since the oxidation reaction may be exothermic.

Advantageously, metal salts (iron, nickel, chromium, copper) are added during the step of generation of the free-radical-donating active species. These metal salts are in particular added to the acid/$H_2O_2$ mixture. The concentration of these salts may vary within a wide range. In particular, the concentration ranges from $10^{-4}$ mol/l to 2 mol/l. They promote the formation in higher concentration of peroxide at the surface of the prosthetic material, in particular of titanium or an alloy thereof, and thus increase the degree of grafting. For example, salts based on iron, nickel, chromium or copper, for instance iron sulfate ($FeSO_4$), iron acetate ($Fe(C_2H_3O_2)_2$), iron bromide ($FeBr_3$), iron iodide ($FeI_2$), iron nitrate ($Fe(NO_3)_3$), iron thiocyanate ($Fe(SCN)_2$, $Fe(SCN)_3$, $Fe_2(SCN)_6$, etc.), may advantageously be added to the acid/$H_2O_2$ mixture. Preferably, iron sulfate is added to the acid/$H_2O_2$ mixture.

Advantageously, a step of obtaining free radicals from the active species generated beforehand at the surface of the material is performed, in particular via thermal reaction of the active species generated. More specifically, the thermal reaction is performed at a temperature of between 25 and 160° C., preferably between 40 and 100° C., even more preferably between 50 and 80° C., more preferably between 60 and 75° C. and most preferably at 70° C.

The free radical production step may be performed before, preferably during, or after the step of placing the monomers in contact with the material onto which active species have been generated.

Thus, in one particular embodiment, the method according to the invention comprises the following steps:
  active species are generated on a prosthetic material as defined above;
  free radicals are generated, in particular by heating between 40° C. and 100° C.; and
  the prosthetic material on which free radicals have been generated is placed in contact with at least one monomer bearing a function allowing a radical polymerization, its radical polymerization allowing the formation of a bioactive polymer, in the absence of oxygen.

According to another embodiment, active species are first generated on the material, which is then placed in contact with monomers under conditions allowing the formation of free radicals from the active species, in particular by heating the monomer solution.

In another particular embodiment of the invention, active species are first generated on the material, which is then placed in contact with a monomer solution, the free radicals then being formed, in particular by heating the monomer solution.

The monomers used in the present method are advantageously grafted onto the abovementioned supports via a radical polymerization reaction. This reaction is initiated via the free radicals generated directly on the support to be grafted.

The monomers used in the method according to the invention comprise at least one group that allows polymerization. Advantageously, the monomers comprise at least one aliphatic unsaturation, preferably a vinyl group, which allows polymerization. According to the present invention, the expression "monomers bearing at least one aliphatic unsaturation" means monomers bearing one or two, preferably one, double or triple bond(s), advantageously a double bond —CH═CH—.

One advantage of the method of the present invention over the indirect method described hereinabove lies in the possibility of grafting a wide variety of polymers. Specifically, any monomer that can be polymerized via a radical polymerization reaction may be used in the present invention.

The structure of the monomers used in the present invention allows the formation of a bioactive polymer at the surface of a prosthetic material. For the purposes of the invention, a polymer is bioactive if it is capable of orienting the eukaryotic and/or prokaryotic cell responses to the site of integration of the prosthetic implant manufactured from a prosthetic material that may be obtained according to the method of the present invention, i.e. if it is capable of promoting osteointegration of the prosthetic implant and of preventing the development of an infection.

In order to improve the osteointegration and antibacterial properties of the materials mentioned above, the monomers used in the context of the present method advantageously comprise a sulfonate and/or carboxylate group. Specifically, it has recently been shown that polymers bearing sulfonate and/or carboxylate ionic groups promote the adhesion, colonization and differentiation of osteoblasts. Furthermore, it has also been shown that polymers bearing these same groups, but even more so when they bear only sulfonate groups, make it possible to inhibit the adhesion of bacterial strains, especially of *Staphylococcus aureus*, which is a strain predominantly involved in infections on prosthetic materials.

It may also be envisioned to graft saccharide groups (glucose, sucrose, fructose, polyose, etc.) or phosphate groups of the type —O—PO—(OH)$_2$, especially of formula (A):

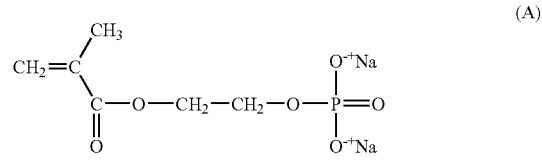

(A)

Preferably, the polymers formed on the prosthetic materials via the method according to the invention are formed from at least one of the following monomers: acrylic acid, methacrylic acid, methyl methacrylate (MMA), N-(sodium phenylsulfonate) acrylamide (NaAS), N-(sodium phenylsulfonate) methacrylamide (NaMS), sodium styrenesulfonate (NaSS), ethylene glycol methacrylate phosphate, methacryloyldiisopropylidene, monomers bearing oside saccharide groups, for instance glucose, glucofuranose, sucrose, polyose, fructose, etc.

The grafted polymers obtained may be homopolymers or copolymers. Thus, in one particular embodiment of the invention, the grafted homopolymers are formed from sodium styrenesulfonate (grafting of polyNaSS) or from methyl methacrylate (grafting of poly(methyl methacrylate) or PMMA).

In one particular embodiment of the invention, the polymers that may be grafted via the method according to the invention are copolymers obtained by radical polymerization of monomers comprising at least one monomer of general formula (I) and at least one monomer of general formula (II), formulae (I) and (II) being as follows:

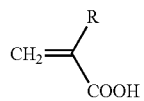

(I)

or a corresponding metal salt

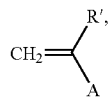

(II)

in which R and R', which may be identical or different, represent a hydrogen atom or a linear or branched $C_1$-$C_6$ alkyl radical and A represents a radical of arylsulfonate or corresponding acid type.

According to one variant of the method according to the invention, the monomers of formula (I) may at the start bear ester functions, and the copolymers thus obtained will then be (partially or totally) hydrolyzed, to obtain the corresponding acid functions.

More specifically, A is chosen from the radicals having the following formulae:

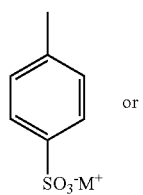

(III)

or

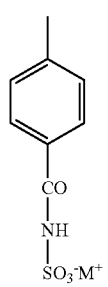

(IV)

in which M represents a metal ion, preferably an alkali metal.

The alkali metal is preferentially chosen from sodium and potassium, advantageously sodium.

Among the linear or branched $C_1$ to $C_6$ alkyl radicals that may especially be mentioned are methyl, ethyl, n-propyl, isopropyl, n-butyl or t-butyl, pentyl and hexyl radicals.

Among the monomers of formula (I) that may especially be mentioned are acrylic acid (AA), methacrylic acid (MA) and ethacrylic acid (EA), the corresponding salts thereof (in particular alkali metal salts, preferably sodium salts), and mixtures thereof. Methacrylic acid is preferred.

Among the monomers of formula (II) that may especially be mentioned are N-(sodium phenylsulfonate) acrylamide (NaAS), N-(sodium phenylsulfonate) methacrylamide (NaMS) and sodium styrenesulfonate (NaSS), and mixtures thereof. Sodium styrenesulfonate is preferred.

By way of illustration, when A of the monomer of formula (II) has the formula (III), the copolymer grafted onto the prosthetic material may be represented more specifically by the general formula (V) below:

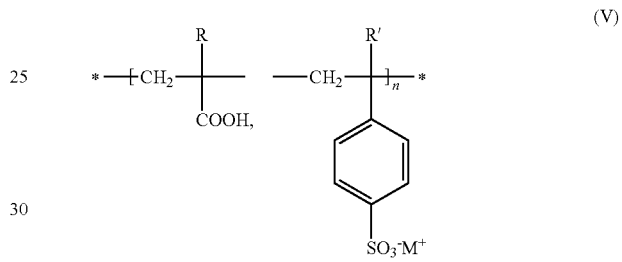

(V)

in which R, R' and M are as defined above, and n represents a real number between 10 and 1000.

The comma means that the amount, the ratio and the sequence of monomer units present in the copolymers vary. This variation is directly linked to the parameters of the polymerization method, for instance the amount of each monomer used.

The molecular weights of the grafted polymers according to the method of the present invention may vary within a wide range and are chosen or controlled by a person skilled in the art as a function of their subsequent application or use. To give an order of magnitude, the weight-average molecular weight may range from 1000 to 100000 daltons.

In this respect, the amounts of the monomers of formulae (I) and (II) may vary within a wide range and depend especially on the properties desired for the copolymers. Preferably, the mole ratio of (I) to (II) ranges from 90/10 to 10/90 and advantageously from 80/20 to 20/80. The copolymers according to the invention in particular have the following mole fractions of (I) to (II): 90/10, 80/20, 70/30, 60/40, 50/50, 40/60, 30/70, 20/80 and 10/90 (these fractions correspond in reality to the fractions of the introduced monomers, the fractions of the monomers incorporated into the copolymers obtained by NMR analysis varying at most by ±2 relative to those mentioned above).

The grafted copolymers according to the method of the present invention may be obtained by radical polymerization of monomers comprising, in addition to the monomers of formulae (I) and (II), other monomers containing at least one aliphatic unsaturation. The other monomers containing at least one aliphatic unsaturation may be of any nature, including monomers giving the grafted polymers a water-soluble or water-insoluble nature. Preferably, the additional monomers are of water-soluble nature, such as monomers bearing a radical of sugar or phosphate type.

Additional monomers that may be mentioned include the monomers having the following formulae:

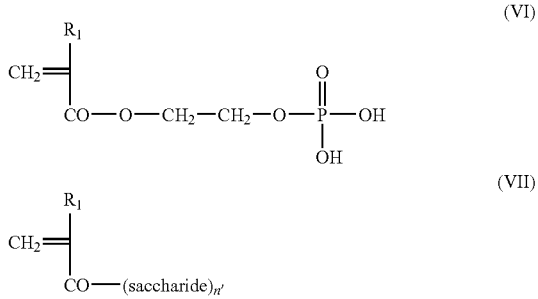

in which $R_1$, which may be identical or different, represents a hydrogen atom or a linear or branched $C_1$-$C_6$ alkyl radical, as defined previously, and n' represents a real number between 10 and 1000. Among the saccharide groups of formula (VII), mention may be made especially of glucose, galactose and sucrose.

In order to preserve the characteristics of the grafted polymers, a person skilled in the art is capable, by means of routine manipulations, of determining the additional monomers that may be envisioned and the amounts thereof.

More particularly, and to give an order of magnitude, the amount of the monomers of formulae (I) and (II) is advantageously greater than or equal to 25 mol % and preferably greater than or equal to 50 mol % relative to the total number of moles of the monomer units present in the polymers.

According to one particular aspect of the invention, the copolymers may be obtained by radical polymerization of the monomers of formulae (I) and (II) alone.

The grafting time may vary within a wide range. A person skilled in the art is capable of selecting the time required for the polymerization on the prosthetic material as a function of its nature, of the polymer to be grafted and of the desired grafting density. A person skilled in the art can select the most appropriate time by measuring the grafting density with toluidine blue (see Example 1.5).

Advantageously, the prosthetic material is placed in contact with the monomer(s) for at least approximately 30 minutes and preferably between approximately 1 hour and approximately 48 hours. More preferably, the prosthetic material is placed in contact with the monomer(s) for more than 2 hours, preferably more than 3 hours, preferably more than 5 hours, preferably more than 8 hours and preferably for approximately 15 hours.

In one preferred embodiment, the invention relates to a method for grafting polyNaSS onto titanium, comprising the following steps:
  free-radical-donating active species are generated at the surface of titanium; and
  the titanium onto which active species have been generated is placed in contact with NaSS at a temperature of between 40 and 100° C., for at least 8 hours, in the absence of oxygen.

In one particularly preferred embodiment, the invention relates to a method for grafting polyNaSS onto titanium, comprising the following steps:
  free-radical-donating active species are generated at the surface of titanium; and
  the titanium onto which active species have been generated is placed in contact with NaSS at a temperature of 70° C., for 15 hours, in the absence of oxygen.

The radical polymerization reaction must take place in the absence of oxygen, since oxygen is an inhibitor of the reaction. Preferably, the reaction is performed in the absence of oxygen, under an inert atmosphere, in particular under argon, helium or nitrogen, advantageously under nitrogen.

After polymerization, the material thus grafted is recovered, and optionally rinsed, especially with water (for example distilled water), especially so as to remove the polymers that have formed but not grafted.

Another subject of the invention concerns prosthetic materials grafted with bioactive polymers that may be obtained according to the method described above.

The invention also relates to the use of a prosthetic material according to the invention for the manufacture of a prosthetic implant, in particular for the manufacture of a joint prosthesis or a dental prosthesis.

An additional subject of the invention relates to prosthetic implants manufactured from the prosthetic materials that may be obtained via the method described above.

The advantages of the present invention will now be detailed in the examples that follow and, as the case may be, in the light of the attached figures.

KEY TO THE FIGURES

FIG. 1: diagram representing the procedure for the direct grafting of NaSS according to the invention.

Figure 2:
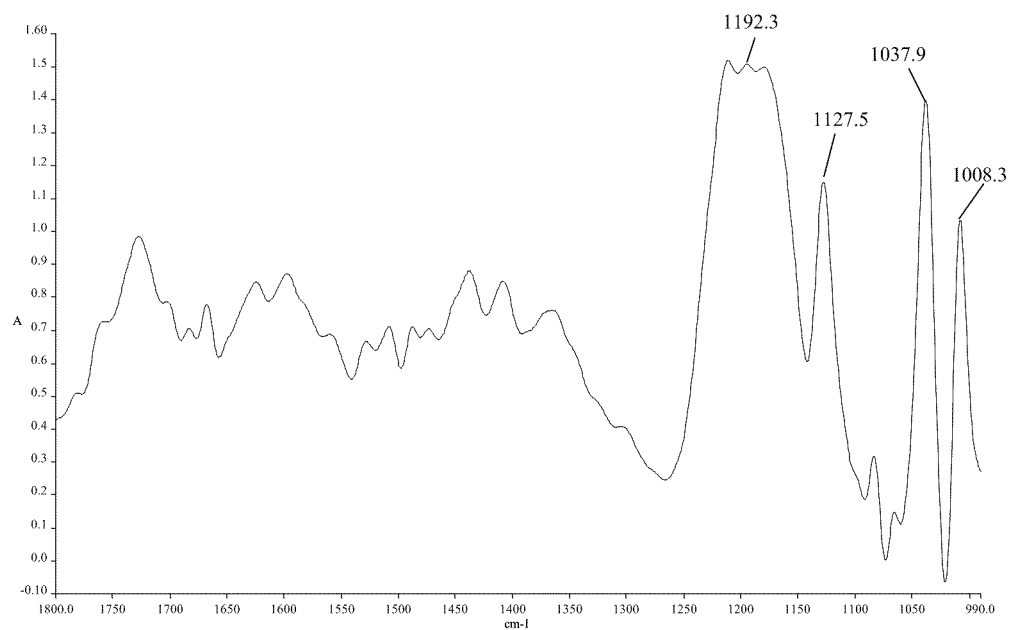

FIG. 2: graph representing the IR spectrum of the surface of titanium chemically oxidized and then grafted with poly-NaSS.

Figure 3A:
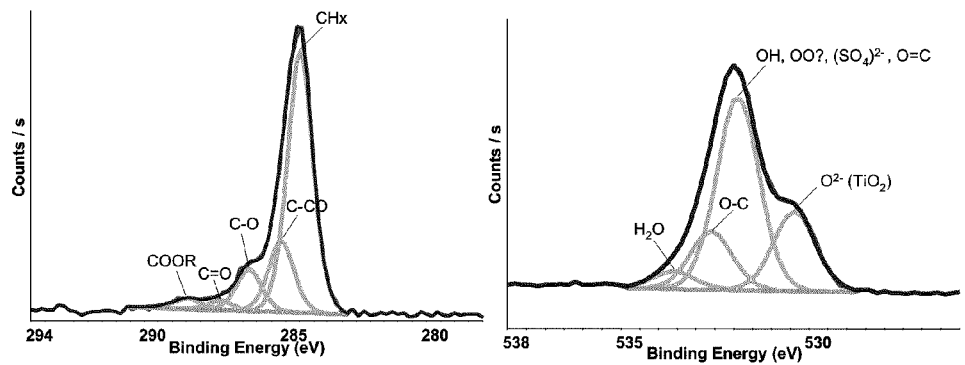

FIG. 3A: deconvolution of the elements carbon C1s (on the left) and oxygen O1s (on the right) of chemically oxidized titanium.

Figure 3B:
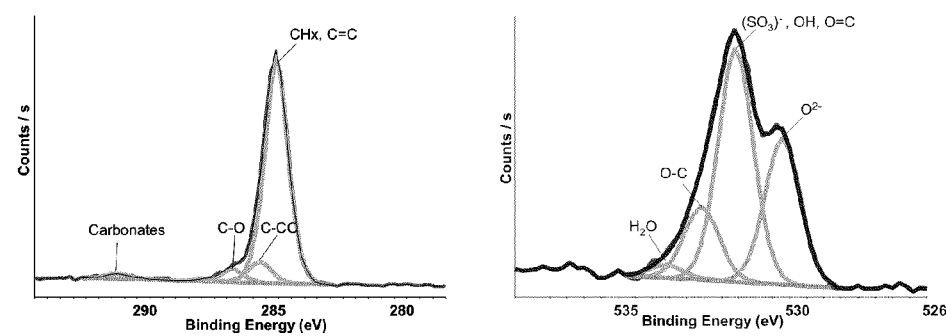

FIG. 3B: deconvolution of the elements carbon C1s (on the left) and oxygen O1s (on the right) of titanium grafted with polyNaSS.

Figure 3C:
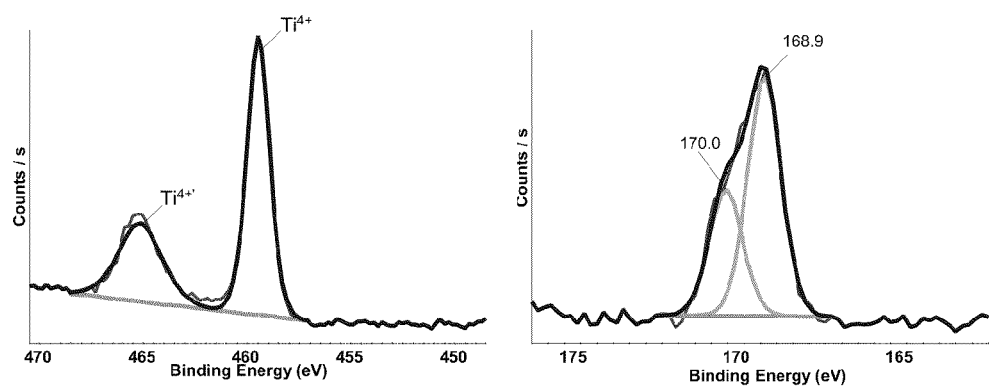

FIG. 3C: deconvolution of the elements titanium Ti2p (on the left) and sulfur S2p (on the right) of chemically oxidized titanium.

Figure 3D:
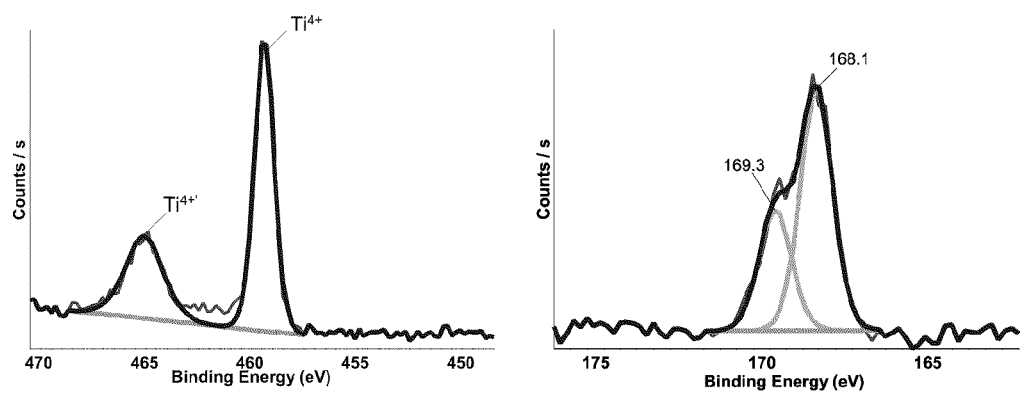

FIG. 3D: deconvolution of the elements titanium Ti2p (on the left) and sulfur S2p (on the right) of titanium grafted with polyNaSS.

Figure 3E:
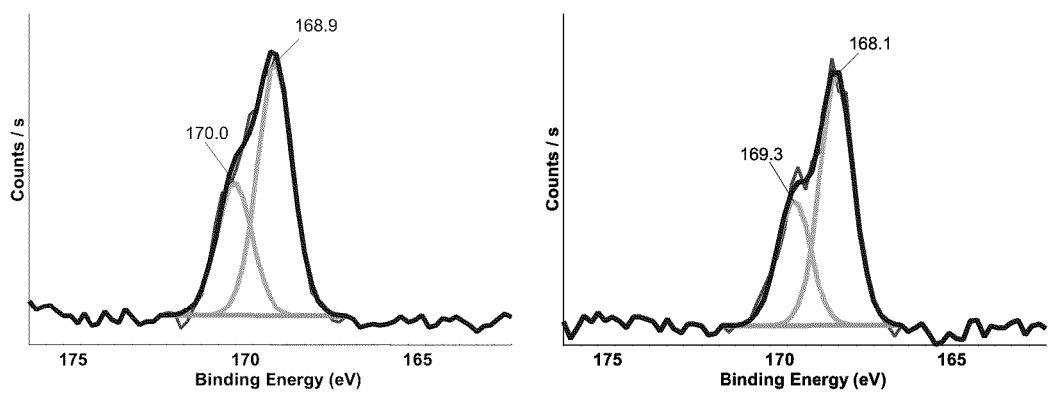

FIG. 3E: comparison of the deconvolutions of the element sulfur S2p of chemically oxidized titanium (on the left) and of titanium grafted with polyNaSS (on the right).

Figure 4:
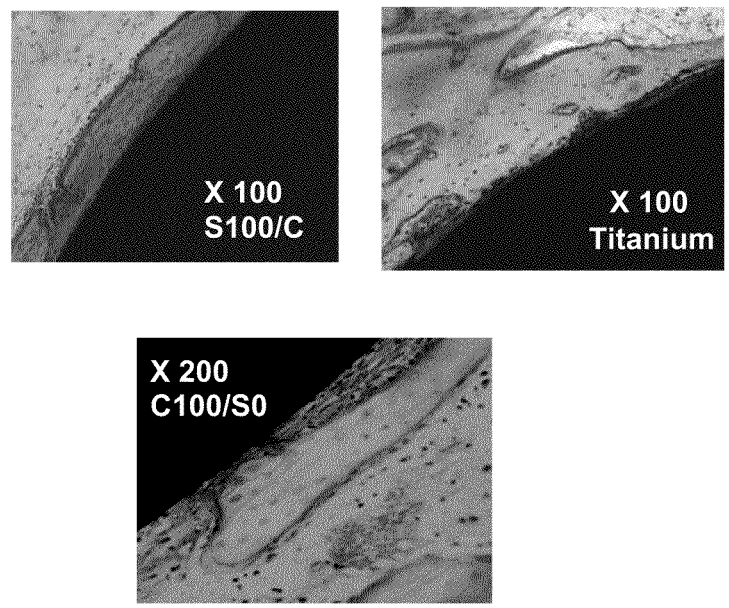

FIG. 4: views in cross section of the newly formed bone surface around implants. S100/0C: 100% sulfonate and 0% carboxylate; C100/S0: 100% carboxylate and 0% sulfonate.

EXAMPLES

Example 1

Grafting of Bioactive Polymer onto the Surface of Titanium Cylinders

The first step was the development of the grafting of the ionic groups. For the sake of simplicity, we chose in a first stage to graft only arylsulfonate groups. The functionalization was performed on titanium disks (99.7% purity) polished beforehand to dispense with problems of roughness.

The grafting of the arylsulfonate groups onto the surface of the titanium was performed via the direct route by creating free radicals via chemical oxidation, which radicals are then used as initiators for the polymerization of a monomer bearing arylsulfonate functions.

The monomer molecule is sodium styrenesulfonate (NaSS). The entire procedure adopted is summarized in FIG. 1.

1.1. Characteristics of the Titanium

The titanium (from the company Alfa Aesar) is in the form of extruded bars 12.7 mm in diameter which have undergone stress-relief annealing for 30 minutes at 700° C. Its purity (Table 1) is 99.7% of nominal composition (grade 1, or T40).

TABLE 1

Chemical composition of the pure titanium used

| Element | | | | | |
|---|---|---|---|---|---|
| C | N | O | H | Fe | Ti |
| Atom % 0.006 | 0.005 | 0.14 | 0.0014 | 0.08 | 99.7676 |

All the studies were performed on disks 2 mm thick, obtained by electroerosion slicing in a water bath, performed by the company Prestasem (Champagne-sur-Seine (77), France). This method of slicing has the advantage of avoiding excessive work-hardening of the material and excessive loss of material, when compared with tower machining, for example.

1.2. Polishing of the Titanium

The mechanical polishing of the disks is performed using an automated arm, mounted on a rotary polisher, with abrasive paper of decreasing granulometries (Struers). A first polishing with abrasive paper of grade 800 (grains of 22 µm) removes about 1/10th of a millimeter of thickness, which has the effect of drawing off the thickness of metal damaged by the pitting due to the method of slicing by electroerosion (electric arc).

The polishing is then refined by using papers of increasingly fine granulometries (1000 and then 1200 papers). The protocol used is as follows: 8 minutes at P800, 4 minutes at P1000, 4 minutes at P1200 (14 µm grains). A surface with a roughness equivalent to that commonly used in the literature for cell behavior studies is obtained.

After polishing, the samples are washed with a pure acetone solution ultrasonically for 10 minutes at room temperature. They are then dried and used immediately, or stored under argon (glove box).

1.3. Purification of the NaSS Monomer

The monomer used to provide the appropriate ionic groups at the surface of the titanium is sodium styrenesulfonate (NaSS, sodium salt of 4-vinylbenzene-sulfonic acid, Aldrich), a vinyl monomer whose chemical formula is represented below

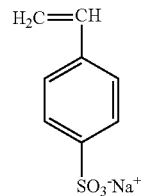

Sodium styrenesulfonate molecule

The sodium styrenesulfonate is purified by recrystallization. This procedure consists in dissolving a mass m of monomer in a water/ethanol mixture in a proportion of 10/90 at a temperature of 60-70° C. The solution is then hot-filtered under water-pump vacuum. The solution thus filtered is placed at 4° C. for 24 hours. The crystals formed are recovered by filtration under vacuum, and then dried at 60-70° C. under vacuum.

1.4 Oxidation and Grafting

The functionalization takes place under a controlled atmosphere of argon (glove box) and may be summarized as follows:

1. Cleaning of the polished titanium surfaces;
2. Formation of peroxide radicals at the surface of the titanium disks by dipping the samples in a 50/50 $H_2SO_4$ (Acros)/$H_2O_2$ (Aldrich) mixture at room temperature. The two reagents are poured simultaneously into the beaker containing the samples, and the whole is stirred for 2 minutes. The reaction is immediate, highly exothermic and is accompanied by an evolution of gas. The initially colorless oxidation solution turns yellow, to orange, then brick red (which is due to the reaction of the sulfuric acid with the titanium and the formation of $Ti^{4+}$ ions).
3. Multiple rinsing of the oxidized surfaces with distilled water;
4. Immersion of the samples in an aqueous solution of NaSS monomer at a concentration of 0.7 M;
5. Heating to 70° C. of the monomer solution in contact with the titanium samples for 14 hours. Heating at 70° C. enables cleavage of the peroxide bond (O-O) into free TiO. radicals, which will serve to initiate the radical polymerization of the vinyl monomers;
6. Rinsing of the metal surfaces grafted with polyNaSS with distilled water in order to remove the homopolymer formed in solution, which is liable to be mixed with the grafted polymer chains.

1.5. Chemical and Physicochemical Characterization a) Assay of the Grafting Density with Toluidine Blue Assay with toluidine blue is a colorimetric technique using the chromophore toluidine blue, which absorbs in the visible region at 633 nm. This molecule has the particular feature of becoming complexed, via its $N^+(CH3)_2$ group, with anionic groups (—$COO^-$). One mole of toluidine blue complexes with one mole of carboxylate group. The toluidine blue assay thus gives the amount of grafted monomer. This property was transposed to NaSS, which can complex with the $N^+(CH3)_2$ group via its sulfonate group (—$SO_3^-$).

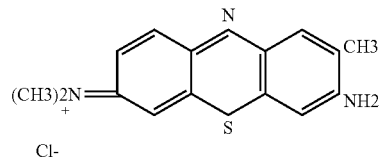

The grafted titanium samples are placed in contact with a $5\times10^{-4}$ M toluidine blue solution (adjusted to pH 10) at a temperature of 30° C. for 6 hours. This step corresponds to the complexation of the toluidine blue to the grafted polyNaSS monomer units. The samples are then rinsed thoroughly with a $1\times10^{-4}$ M sodium hydroxide solution, to remove the non-complexed toluidine blue. The rinsing is stopped when the solution is colorless.

The complexed toluidine blue is then decomplexed using 50% acetic acid solution (Acros Organics) which is left in contact with the titanium samples for 24 hours.

The solution obtained is assayed by spectrophotometry using a spectrophotometer of Safas Xenius type driven by its software. The coefficient of molar extinction ε of the toluidine blue is equal to 51 230 L·mol$^{-1}$·cm$^{1}$.

From the calculated concentration/the amount of grafted molecules is calculated using the following equation:

$$m = [Monomer] \times V \times M_{monomer} \text{ (in g)}$$

with V=volume of the assayed solution (5×10$^{-3}$ L)
$M_{monomer}$=molar mass of the monomer NaSS The surface area of a pellet measures 1 cm$^2$, thus this mass of grafted monomer may be expressed as an amount of grafted material in g/cm$^2$ for one pellet face. The measured optical density gives an amount of grafted molecules of about 10 μg/cm$^2$.

The assayed samples were then rewashed several times with water and their complexation with toluidine blue was assayed up to four times. The measured grafting density then fell to 3 μg/cm$^2$, and stabilized at this value. The phenomenon outlined previously may explain this observation: specifically, the complexation with toluidine blue possibly resulted in distortion of the polymer chains and the multiple washes performed made it possible to remove the intermeshed chains not really grafted.

The grafting density obtained with the method according to the invention is an extremely high density, since the values obtained in the literature with the indirect method via silanization are rather of the order of 0.1 to 0.2 μg/cm$^2$.

b) Attenuated Total Reflection Fourier Transform Infrared Spectroscopy (ATR/FTIR)

FTIR spectroscopy in attenuated total reflection (ATR) mode was used to analyze the surface of our titanium samples. The FTIR spectrophotometer used to take the measurements is a Nicolet Avatar 370-FTIR machine. The samples are analyzed in ATR mode. For the measurements, the wavelengths are scanned between 4000 and 650 cm$^{-1}$, in 4-cm$^{-1}$ a steps, with a resolution of 1 cm$^{-1}$. The oxidized or unoxidized, grafted or ungrafted titanium samples are applied with a calibrated force against the crystal, in order to ensure maximum contact between the sample and the diamond; 120 acquisitions are accumulated per point, to minimize the background noise. The background is taken on the atmosphere.

Table 2 below summarizes the main characteristic absorption bands of polyNaSS and their assignments to the various chemical groups.

TABLE 2

Characteristic IR absorption bands of polyNaSS

| Frequency (cm$^{-1}$) | Appearance of the peak(s) | Assignment |
|---|---|---|
| 1640-1600 and 1496-1433 | weak | ν (C═C) of the aromatic nucleus |
| 1410 | medium | ν (SO$_2$) |
| 1180-1127 | strong | SO$_3^-$Na$^+$ (salt) |
| 1040 | strong | ν (O═S═O) |
| 1009 | strong | aromatic nucleus |

The characteristic peaks of the vibrations of the sulfone group O═S═O and of the aromatic nucleus of the NaSS molecule constitute a doublet located at 1009-1040 cm$^{-1}$; the peaks located at about 1127 and 1180 cm$^{-1}$ may be attributed to the absorption of the sulfonic acid salt. The antisymmetric valency vibration of the SO$_2$ group corresponds to the peak at 1410 cm$^{-1}$ and a shoulder of the preceding peak at about 1220 cm$^{-1}$ is noted, which corresponds to the symmetrical valency vibration of the SO$_2$ group. As regards the series of peaks between 1640 and 1430 cm$^{-1}$, this may be attributed to the valency vibrations of the (>C═C<) bonds of the benzene nucleus.

The infrared spectrum of the chemically oxidized and grafted titanium surface of this same product is shown in FIG. 2.

The presence of polyNaSS on this surface is especially confirmed by the two characteristic peaks at 1008 and 1040 cm$^{-1}$. The absorption of the sulfonic acid salt at about 1127-1180 cm$^{-1}$ is also found. On the other hand, the valency vibrations of the SO$_2$ group and of the C═C double bonds of the aromatic nucleus are buried in the background noise, given the difference in intensities between the pure polyNaSS product in powder form and the product grafted onto the surface.

c) Chemical Analysis Via Photoelectron Spectroscopy (XPS)

The samples were analyzed with an Escalab VG 220i-XL spectrometer. The X-rays are produced via a monochromatic AlKα source of 1486.6 eV.

The samples are introduced four by four into the analysis chamber, which is pumped under ultra-high vacuum (10$^{-9}$ to 10$^{-10}$ mbar). The emission angle used is 45°, for a surface analysis depth of 10 nm at full depth (the detector being placed normal to the sample). The diameter of the pointing on the sample is from 150 to 200 μm (power of about 70 W, incident beam 10 kV).

The analysis of each sample begins by acquiring an overall spectrum, by scanning the entire domain of the binding energies, in order to identify the main chemical elements present at the surface of the sample, and which will each subsequently be analyzed in greater detail. The given energy resolution is ±0.1 eV.

As regards the analysis of the simply oxidized samples, the main elements are carbon, oxygen and titanium; for the grafted samples, sulfur and sodium (NaSS) are also detailed. The deconvolutions are performed with the Eclipse software supplied by VG; the reference is taken on the main peak of the $C_{1s}$ contribution of carbon, which is set at a binding energy of 284.8 eV.

The chemical composition of the chemically oxidized and grafted titanium surfaces is given in Table 3.

TABLE 3

Chemical composition of the titanium surfaces

| | Atom % ± SD | | | | | |
|---|---|---|---|---|---|---|
| | C | O | Ti | S | Na | Pollutants |
| Polished Ti control P1200 | 33.2 ± 4.4 | 46.4 ± 2.1 | 14.7 ± 0.4 | — | — | 5.4 ± 2.2 |

TABLE 3-continued

Chemical composition of the titanium surfaces

| | Atom % ± SD | | | | | |
|---|---|---|---|---|---|---|
| | C | O | Ti | S | Na | Pollutants |
| Chemical oxide $H_2SO_4/H_2O_2$ | 34.2 ± 2.6 | 47.0 ± 1.6 | 7.4 ± 0.8 | 7.8 ± 1.7 | — | 2.7 ± 0.6 |
| Chemical oxide grafted with pNaSS | 53.8 ± 1.3 | 30.3 ± 1.9 | 5.0 ± 1.4 | 5.8 ± 0.9 | 3.8 ± 0.8 | 1.2 ± 0.4 |

The overall surface composition of the chemical oxide is virtually the same as that of the native control oxide, with the exception of the atomic percentage of titanium, which is lower: thus, the percentages of carbon and oxygen are, respectively, 33% and 46% for the native oxide and 34% and 47% for the chemical oxide. On the other hand, the atomic percentage of titanium falls from 15% to 7% after chemical oxidation. In fact, the detected amount of titanium decreases in "relative proportion" on account of the substantial presence of sulfur contamination. This sulfur detected in large amount (8 atom %) on the oxidized samples is probably a residue of the oxidation bath that contains sulfuric acid, which persists despite all the rinses performed.

The analysis of the change in atomic composition between the oxidized state and the grafted state of polyNaSS makes it possible to make the following observations:

The atomic percentage of carbon increases by a factor of 1.6, and rises from 34% for the chemical oxide to 54% for the grafted oxide.

In parallel, the percentage of oxygen decreases by a factor of 1.6, and its contribution falls from 47% to 30%. Consequently, the ratio C/O rises from 0.7 for the oxide alone to 1.8 for the oxide grafted with polyNaSS. This appears to be logical, given that the added NaSS molecules contain little oxygen compared to carbon.

The contribution of titanium also decreases from 7.4% to 5%, since the oxide is masked and the titanium is detected with greater difficulty under the thickness of grafted polymer.

Appearance of sodium (4%), and maintenance of the percentage of sulfur at 6%, compared with the oxide alone (8%).

These results confirm that polymerization of the NaSS has taken place and that polyNaSS is indeed present at the surface of the titanium.

Moreover, the ratio of the Na/S atomic percentages oscillates between 0.6 and 0.7, whereas, in all logic, it should be 1. This may be explained by the fact that the sodium styrenesulfonate NaSS is a salt which is dissociated in aqueous medium, and it is thus possible that the sodium is complexed with another counterion.

The deconvolutions of the various contributions of the elements C1s, O1s, Ti2p and S2p of the chemically oxidized and polyNaSS-grafted samples are given in FIGS. 3A-3E.

The shape of the deconvolution of the C1s spectrum of carbon (on the left) of the grafted oxide (FIG. 3B) substantially resembles that of the ungrafted oxide (FIG. 3A). However, the very high percentage of hydrocarbon-based species at 284.6 eV is attributed to the carbon chain and to the rings of the grafted polyNaSS (CHx and C=C bonds). This contribution now represents virtually all (85%) of the carbon present.

The rest is shared between the components bonded to oxygen, in much lower intensities than previously (15% of the carbon present as opposed to 35% for the oxide alone).

On the O1s spectrum of oxygen (on the right), the usually hydroxyl contribution at 532 eV is shifted towards lower energies at 531.5 eV. It may then be attributed to the $SO_3^-$ ions of the functional groups on the polyNaSS rings; this component (50% of the oxygen present) also includes the carbonyls C=O and potentially some of the hydroxyls OH if they are still present.

The deconvolution of the spectrum of Ti2p (on the left) of the grafted oxide (FIG. 3D) has the same shape as with the ungrafted oxide (FIG. 3C), with a single component Ti(IV) and even less intense, since the titanium present in the $TiO_2$ oxide has become distant from the analyzed zone, masked by the layer of polymer.

The position of the sulfur peak at 168.1 eV (with the correspondence on O1s at 531.5 eV) shows that sulfur is present in the form of sulfonate ions $SO_3^-$. The $S2p_{1/2}$ peak is positioned with a $\Delta$ in energy of 1.18 eV, i.e. at about 169.3 eV.

FIG. 3E reports for comparative purposes the $S2p_{3/2}$ spectra of sulfur, obtained, respectively, on the chemical oxide alone (on the left) and the grafted chemical oxide (on the right). The shift in position of the $S2p_{3/2}$ peak from 168.9 eV to 168.1 eV between the oxidized and grafted states is easily observed. This confirms that the sulfur of the polyNaSS-grafted sample is present in the form of sulfonate ions $SO_3^-$ rather than sulfate $SO_4^{2-}$, which again confirms the grafting of the polyNaSS.

The Na1s peak of sodium emerges at an energy of 1072 eV.

d) Surface Energy by Measuring the Contact Angle

A drop of liquid is placed on a surface, and after obtaining the equilibrium position, the angle between the tangent of the drop and the surface is determined using a goniometer.

The contact angle measurements were taken by means of the "deposited drop method", in static mode, using a DSA 10 machine (Kruss). The surface energy was deduced from the measurements of these angles via the Owens-Wendt method.

$$\frac{\gamma_L(\cos\theta + 1)}{2\sqrt{\gamma_L^d}} = \sqrt{\gamma_S^p} * \sqrt{\frac{\gamma_L^p}{\gamma_L^d}} + \sqrt{\gamma_S^d}$$

$$\frac{\gamma_L(\cos\theta + 1)}{2\sqrt{\gamma_L^d}} = \sqrt{\gamma_S^p} * \sqrt{\frac{\gamma_L^p}{\gamma_L^d}} + \sqrt{\gamma_S^d}$$

0.5-µL drops of different solvents are placed on the surfaces: distilled water, formamide (99.5%, Aldrich), ethylene glycol and diiodomethane. The measurements are taken once the equilibrium state has been reached after depositing each drop, i.e. about 5 seconds. At least six zones of the surface on two different samples produced according to the same protocol are thus photographed to check the homogeneity of the surfaces studied. The experimental error is estimated at ±2°. The results of the measurements are given in Table 4.

TABLE 4

Contact angles measured on the titanium
surfaces chemically oxidized and directly grafted
with polyNaSS

| Contact angles | Water | Formamide | Ethylene glycol | Diiodomethane |
|---|---|---|---|---|
| Titanium control | 59 ± 5 | 35 ± 5 | 38 ± 5 | 48 ± 5 |
| Chemical oxide | 31 ± 7 | 18 ± 4 | 20 ± 6 | 30 ± 6 |
| Chemical oxide + pNaSS | 16 ± 5 | 18 ± 5 | 17 ± 4 | 40 ± 5 |

A decrease in the value of the contact angle with water is found on passing from the control titanium to the titanium grafted with polyNaSS, due to the hydrophilic nature of the polyNaSS.

From the contact angle values, the corresponding surface energies were calculated via the Owens-Wendt method (Table 5).

TABLE 5

| Surface energy | Overall surface energy γ (mN/m) | Dispersive component $\gamma^d$ (mN/m) | Polar component $\gamma^p$ (mN/m) |
|---|---|---|---|
| Titanium control | 44.3 (±2.3) | 27.7 (±1.1) | 16.5 (±1.2) |
| Chemical oxide | 59.2 (±2.3) | 26.1 (±1.0) | 33.1 (±1.3) |
| Chemical oxide + pNaSS | 64.9 (±1.9) | 16.9 (±0.7) | 47.9 (±1.2) |

It is found that the overall value of the surface energy increases more and more on passing from the polished titanium to the titanium grafted with polyNaSS. Thus, it rises from 44.3 mN/m for unmodified titanium to 59.2 mN/m for oxidized titanium, and to 64.9 mN/m for grafted titanium. This increase is mainly due to the increase in the polar component of the energy, the contribution of which is multiplied by 2 between the unmodified and oxidized states; this same contribution increases practically by a factor of 3 between the unmodified and grafted states, whereas that of the dispersive component decreases at the same time by a factor of 1.6.

The chemical oxidation with hydrogen peroxide in fact causes the appearance of TiOH groups, thus increasing the hydrophilic nature of the surface of the titanium.

Next, the grafting of the polyNaSS slightly increases the surface energy when compared with the chemically oxidized titanium. The surface energy rises from 59.2 to 64.9 mN/m, NaSS being a polar molecule by virtue of its ionic sulfonate group, and bearing three oxygen atoms.

Additional Experiment:

The grafting of polymethyl methacrylate (PMMA) was performed in an identical manner to that of polyNaSS. Measurement of the contact angle of a drop of water on the titanium grafted with PMMA gave a value of 65°, close to the value of 70° obtained on pure PMMA. This experiment confirms that it is possible to graft various polymers onto the surface of titanium.

Example 2

Improvement in the PolyNaSS Grafting Density

In order to optimize the amount of polymer grafted onto titanium, various parameters were modified in the method of Example 1 above. Thus, a density as high as 15.4 μg/cm², as measured by assaying with toluidine blue, was obtained with the following parameters (method A):

oxidation using a sequential mixture: $H_2SO_4$ for 1 minute and then $H_2O_2$ for 2 minutes;
use of iron sulfate as catalyst in the $H_2SO_4/H_2O_2$ mixture; and
polymerization reaction at 70° C. for 15 hours.

With such a method, the grafting density obtained is particularly high compared with the densities that may be obtained with the indirect method via silanization of the prior art. Furthermore, the grafting obtained with method A is stable since, after one month, no loss of polymer at the surface of the titanium was observed (Table 6).

TABLE 6

Stability of the grafting via method A

| | Grafting density (μg/cm²) 1 day | Grafting density (μg/cm²) 2 days | Grafting density (μg/cm²) 1 month |
|---|---|---|---|
| Method A | 15.4 ± 3.8 | 15.5 ± 3.5 | 15.5 ± 3.4 |

Example 3

Cellular Activity on Contact with Modified Surfaces

A) Development of Osteoblasts at the Surface of Modified Titanium

The cells chosen to study the cellular activity on contact with modified titanium surfaces belong to a line derived from human osteoblasts MG-63. We performed measurements of adhesion, of alkaline phosphatase activity and of amounts of precipitated calcium phosphate.

The adhesion measurements on the MG63 cells were taken after 30 minutes of incubation under a constant force of 140 dynes/cm². It is found that the percentage of detached cells decreases from the oxidized titanium (14%) to the polyNaSS-grafted titanium (8%). The polyNaSS-grafted surfaces improve the adhesion although their hydrophilic nature is of a level relatively close to that of the surfaces that have only been oxidized.

Adhesion measurements taken 4 hours after incubation show similar results, although the differences are less pronounced.

The cellular differentiation was also studied by means of two main markers: the alkaline phosphatase activity and the mineralization.

The first step was to measure the alkaline phosphatase activity of the cells for the primordial role of this enzyme in bone formation and its inductive effect on mineral deposition, since it regulates phosphate transport. The presence of poly-NaSS grafted onto the surface of titanium significantly increases the alkaline phosphatase activity by about 25% compared with the oxidized titanium surface.

The second step of the differentiation is characterized by the formation of bone and of mineral deposit: calcification. The calcium phosphate assay was thus performed to determine the stage of differentiation reached by the osteoblasts MG-63. It was found that the amounts of calcium extracted from the cells increased significantly (about 30%) when the supports were grafted with polyNaSS, when compared with the oxidized surfaces.

The final results obtained concern the implantation of a titanium prosthesis modified with either polyNaSS or polymethacrylic acid or a mixture of the two polymers. These preliminary tests were performed with samples of titanium that were not characterized as fully as the polyNaSS-grafted samples during the study of adhesion of human osteoblasts MG-63. The aim of the study was to evaluate in vivo the tissue response of titanium grafted with sulfonate or carboxylate groups. To achieve this objective, modified or unmodified titanium cylinders were implanted into the femoral condyle of rabbits, which were sacrificed after 4 weeks. A quantification of the newly formed bone surface around the implants is evaluated using a slice of each sample, by means of an image analyzer (FIG. 4).

Semi-quantitatively, it may be noted that, on the sample covered with polyNaSS, the bone is uniformly distributed along the bone surface with relatively broad contact surfaces. No fibrous tissue and cartilaginous nodules are observed, in contrast with the unmodified titanium implants.

For the composition that contains only carboxylate groups, the contacts between the bone and the implant are present, but the surfaces are smaller and less numerous. There are zones of fibrous tissue in contact with the implanted surface that contain giant cells.

The presence of the sulfonate groups increases the amount of bone tissue in contact with the implant. Conversely, the presence of carboxylate groups promotes the formation of fibrous tissue.

A more quantitative evaluation of the bone/implant contact was performed by histomorphometry. The mean percentage of bone/implant contact for the unmodified titanium was 32%, and 38% for the sulfonate-modified titanium. The percentage of contact decreases greatly for the implant covered with carboxylate groups (12%). The percentage of cartilage/implant contact ranges from 1.3% for titanium $SO_3^-$ to 8% for carboxylated titanium. The important point is that the percentage of bone+cartilage contact for the sulfonated titanium is higher than that measured for the unmodified titanium.

B) Inhibition of Bacterial Adhesion

On the subject of bacterial adhesion, a few measurements with *Staphylococcus aureus* were taken. We measured levels of inhibition of bacterial adhesion of 79% when compared with polished titanium, and 54% when compared with oxidized titanium. These very encouraging preliminary results confirmed those obtained during measurements of adhesion of *Staphylococcus aureus* and *Streptococcus pyogenes* on polyNaSS. They were recently confirmed on silicone implants covered with sulfonate groups, which made it possible to reduce in vivo the bacterial adhesion by 2 log units.

The invention claimed is:

1. A titanium or titanium alloy prosthetic material onto which is grafted a poly(sodium styrene sulfonate) polymer (polyNaSS polymer), wherein said polyNaSS polymer is grafted directly at the surface of said titanium or titanium alloy prosthetic material via an oxygen-carbon covalent bond.

2. A prosthetic implant comprising a prosthetic material according to claim 1.

3. A joint prosthesis comprising a prosthetic material according to claim 1.

4. A prosthetic implant according to claim 2, wherein said implant is a dental prosthesis.

5. A prosthetic implant, characterized in that it is manufactured from a prosthetic material according to claim 1.

6. The titanium or titanium alloy prosthetic material according to claim 1, wherein the titanium alloy is a nickel, vanadium, aluminum or molybdenum alloy.

7. A prosthetic implant according to claim 2, wherein said implant is a hip prosthesis.

8. A titanium or titanium alloy prosthetic material onto which is grafted a poly(sodium styrene sulfonate) polymer (polyNaSS polymer), wherein said polyNaSS polymer is grafted directly at the surface of said titanium or titanium alloy prosthetic material via an oxygen-carbon covalent bond, said grafted titanium or titanium alloy prosthetic material being obtained according to the following steps free-radical-donating active species are generated at the surface of the titanium or titanium alloy prosthetic material; and the titanium or titanium alloy prosthetic material onto which active species have been generated is placed in contact with sodium styrene sulfonate (NaSS), the polymerization is initiated from the titanium or titanium alloy prosthetic material by heat-induced polymerization wherein free radicals are formed on the surface of said titanium or titanium alloy prosthetic material by thermal reaction at a temperature comprised between 40° C. and 100° C., in the absence of oxygen, wherein the free radicals formed at the surface of the titanium or titanium alloy prosthetic material are the only polymerization initiators;

whereby polymerization chain progresses from the titanium or titanium alloy prosthetic material.

* * * * *